United States Patent [19]

Bellingham

[11] Patent Number: 5,066,299
[45] Date of Patent: Nov. 19, 1991

[54] QUICK USE SUTURE PACKAGE

[75] Inventor: Godfrey Bellingham, Lake Elmo, Minn.

[73] Assignee: Bellingham Medical, Inc., Lake Elmo, Minn.

[21] Appl. No.: 545,845

[22] Filed: Jun. 29, 1990

[51] Int. Cl.[5] ............................................. A61B 17/06
[52] U.S. Cl. .................... 606/213; 206/440; 206/441
[58] Field of Search ............ 206/440, 441, 438, 820, 206/63.3; 606/215, 213; 128/155, 156

[56] References Cited

U.S. PATENT DOCUMENTS

| | | | |
|---|---|---|---|
| 114,750 | 5/1871 | Battersby | 606/215 |
| 2,244,448 | 6/1941 | Eaton | 606/215 |
| 2,292,995 | 8/1942 | Greenwall | 206/441 |
| 2,522,963 | 4/1950 | Rogers | 206/441 |
| 2,815,126 | 12/1957 | Deckers | 206/441 |
| 2,818,865 | 1/1958 | Jacoby | 606/215 |
| 3,086,531 | 4/1963 | Schütz | 606/215 |
| 3,162,306 | 12/1964 | Zackheim | 206/440 |
| 3,357,425 | 12/1967 | Morgan | 206/440 |
| 3,402,716 | 9/1968 | Baxter | 606/215 |
| 3,759,376 | 9/1973 | Lisowski | 206/63.3 |
| 4,222,383 | 9/1980 | Schossow | 606/215 |
| 4,264,008 | 4/1981 | Kozlow | 206/441 |
| 4,605,005 | 8/1986 | Sheehan | 606/215 |
| 4,666,040 | 5/1987 | Murata | 206/440 |
| 4,807,753 | 2/1989 | Goldstein | 206/441 |
| 4,884,563 | 12/1989 | Sessions | 206/441 |

OTHER PUBLICATIONS

Golden, Theodore et al., "Primary Healing of Skin Wounds and Incisions with a Threadless Suture", vol. 104, Oct. 1962, American Journal of Surgery, pp. 603–611.

Primary Examiner—Stephen C. Pellegrino
Assistant Examiner—Gary Jackson
Attorney, Agent, or Firm—Jacobson & Johnson

[57] ABSTRACT

A suture package for holding a plurality of different groups of wound closure strips in a visually comparative position to enable a user to quickly select and apply the appropriate wound closure strip for closing a wound and a backing strip that extends beyond the end of the wound closure strip to inhibit air from drying out the adhesive on the end of the wound closure strips.

8 Claims, 2 Drawing Sheets

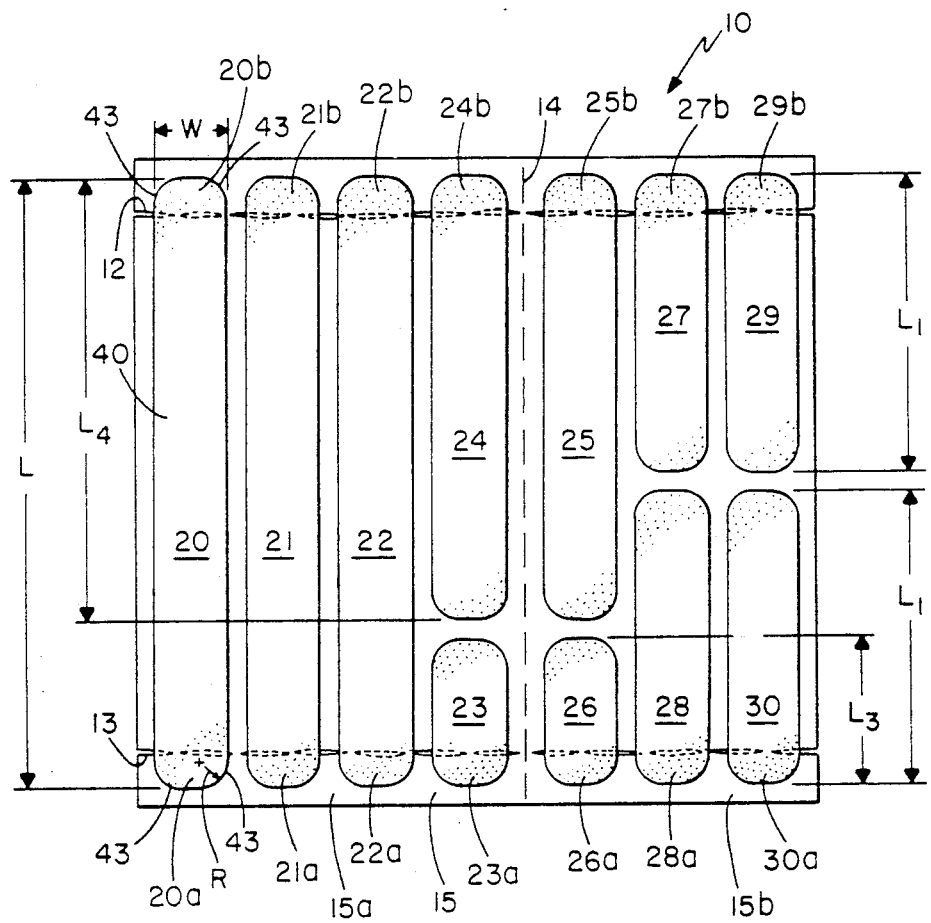
FIG. 1
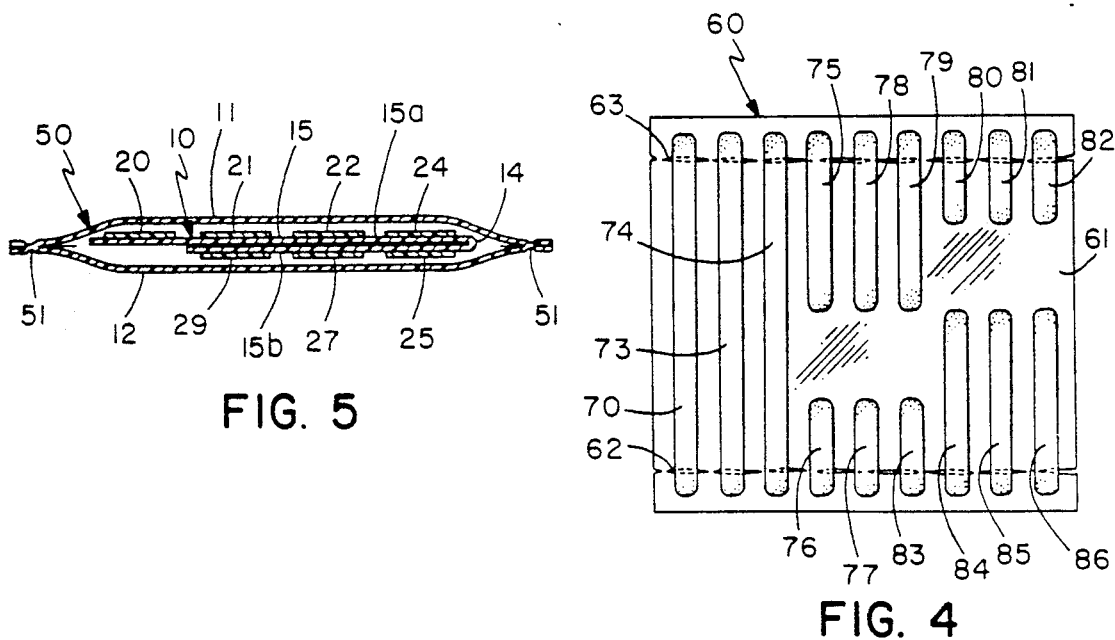
FIG. 5
FIG. 4

QUICK USE SUTURE PACKAGE

FIELD OF THE INVENTION

This invention relates generally to sutures or wound closure strips and, more specifically, to improvements to wound closure strips and packages of wound closure strips that enable a user to quickly select the correct length wound closure strip for use in closing a wound or incision.

BACKGROUND OF THE INVENTION

Typically, wound closure strips are sold in sterilized packages with the wound closure strips having an elongated rectangular shape. The wound closure strips are mounted on backing cards with a number of wound closure strips of the same length located in a side by side relationship on the backing card. To attach a wound closure strip to a wound the surgeon must either cut the wound closure strip to proper length with a scissor or use the packaged pre-cut wound closure strip. Since the wound closure strip contains an adhesive backing, cutting the wound closure strip may cause the adhesive and the wound closure strip to adhere to the scissors thus making it difficult to cut the wound closure strip. The present invention provides a package of wound closure strips having rounded edges that are located in a side by side arrangement to quickly allow a surgeon to estimate what length of wound closure strip is necessary and then remove and place the sterile wound closure strip directly on the wound without having to cut or trim the wound closure strip. In addition the use of radiused corners on the wound closure strip ends substantially reduces the chances of the users clothing or other bandages from accidently pulling the corner of the wound closure strip loose from the patients skin.

DESCRIPTION OF THE PRIOR ART

U.S. Pat. No. 4,222,383 shows a suture combined with a surgical drape with the suture having polymeric coated strong flexible wires that are twisted together.

U.S. Pat. No. 2,244,448 shows a surgical stitch with a reduced portion for placing over the wound or incision to prevent the adhesive from sticking to the wound.

U.S. Pat. No. 2,292,995 shows a package of equal length bandages with the protective backing being entirely separated from its adjacent bandages.

U.S. Pat. No. 2,522,963 shows a package of adhesive bandages where the bandages are sealed in individual compartments in the package.

U.S. Pat. No. 2,815,126 shows a bandage package which is hermetically closed, deformable, and practically air and water tight that is carried in a wallet like container.

U.S. Pat. No. 3,086,531 shows a surgical adhesive plaster for closing wounds with the strip having a set of parallel spaced openings in the central region of the strip that extends over the wound.

U.S. Pat. No. 3,402,716 shows an adhesive backed wound closure strip having a backing strip with the regions of the backing strip located outside the weakened areas being free of adhesive. The wound closure strip also includes a semi-stiff backing strip that remains relatively straight as the wound closure strip is peeled off the backing strip.

U.S. Pat. No. 3,759,376 shows a suture package for double armed multi-strand sutures that contains pins for winding the sutures around.

U.S. Pat. No. 4,605,005 shows a package of wound closure strips where the center portion of the wound closure strip has a convex-curve to fit over the drawn together edges of a wound.

U.S. Pat. No 4,264,008 shows an adhesive bandage and package that permits one to fold the bandage directly onto the wound without unnecessary separate handling of the bandage.

U.S. Pat. No. 4,807,753 shows a dispenser and packaging for bandage strips where the bandages are located in separate packages that are connected together in an end to end relationship by a line of weakness that permits a user to separate one package from another without opening the adjacent package.

U.S. Pat. No. 4,884,563 shows a non-strectchable wound dressing made from a series of overlapping continuous strips.

BRIEF DESCRIPTION OF THE DRAWINGS

FIG. 1 shows a plurality of different length wound closure strips located on a foldable backing sheet;

FIG. 4 shows a plurality of wound closure strips located on a backing sheet; and FIG. 5 shows a cross sectional view taken along lines 5—5 of FIG. 2.

SUMMARY OF THE INVENTION

Figure 3:
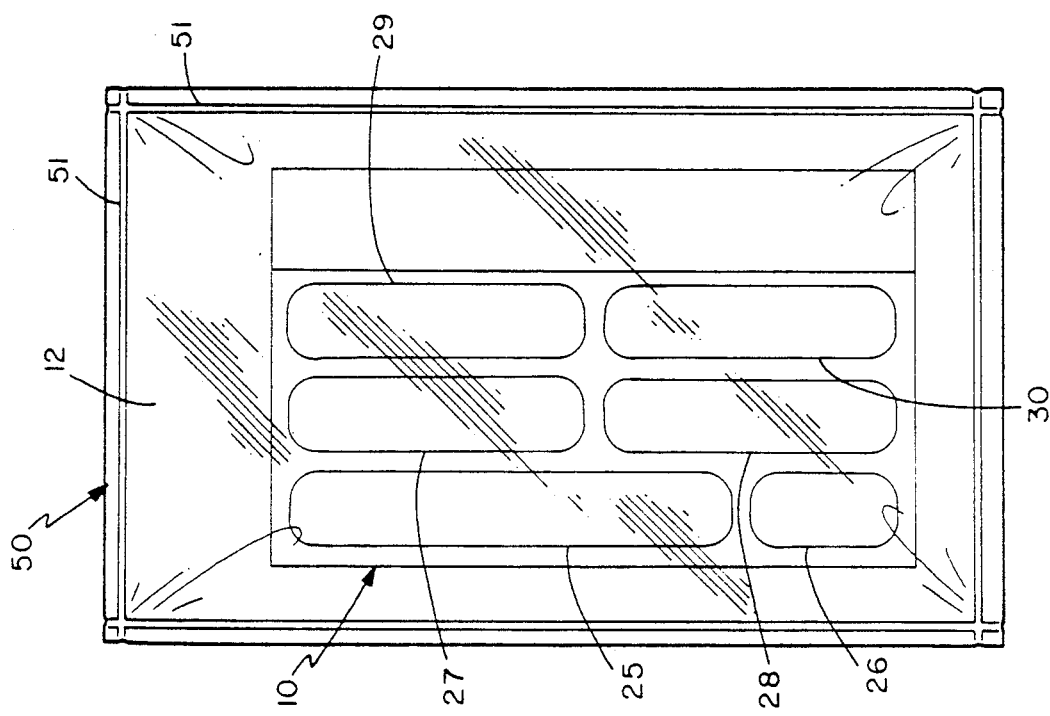
FIG. 3 shows a back view of package of multiple length wound closure strips.
Figure 2:
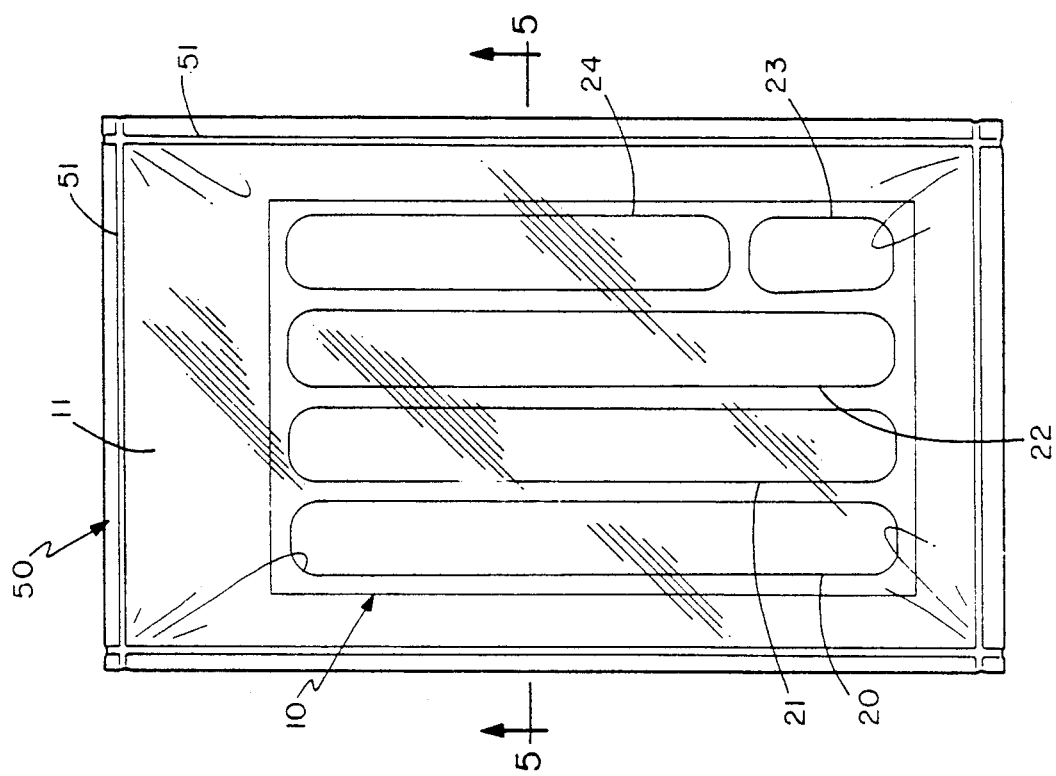
FIG. 2 shows a front view of a package of multiple length wound closure strips.

Briefly, the present invention comprises an improvement to wound closure strips and packages of wound closure strips that assists the user in quickly selecting and applying the proper length suture to a wound without the user having to cut the wound closure strip to length. In addition, the packaging of the wound closure strips in a spaced relationship from the edge of the backing card permits the wound closure strips to be stored and used at a later date without loss of effectiveness of the adhesive on the wound closure strip.

DESCRIPTION OF THE PREFERRED EMBODIMENT

Referring to FIG. 1 reference numeral 10 identifies a backing strip containing a plurality of different length wound closure strips located in a parallel spaced relationship on backing release card 15 having a first portion 15a and a second portion 15b that are foldable along a fold line 14. Backing release card 15 typically comprises a silicone coated stiff paper that holds the wound closure strips in a parallel spaced relationship with the coating permitting a user to peel an adhesive backed wound closure strip from the backing card. Located on one end of backing card 15 is a first line of weakness 12 and located along the opposite end of backing card is a second line of weakness 13. Typically, the line of weakness comprise a series of elongated perforations in the backing card that permit removal of either card end to expose the end of the wound closure strips.

Reference numerals 20, 21, and 22 identify a group of first wound closure strips having a width W and a length L. Typically, the width may range from 0.125 inches to one inch and the length from 0.63 inches to five inches.

Reference numerals 20a, 21a, and 22a identify the end portion of wound closure strips 20, 21, and 22 that extend beyond line of weakness 13 and reference numerals 20b, 21b, and 22b identify the end portion of the wound closure strips that extend beyond line of weakness 12.

Similarly, reference numerals 24 and 25 identify a second group of wound closure strips of length $L_4$ and reference numerals 23 and 26 identify a third group of wound closure strips having a length $L_3$. The combined length of wound closure strips 23 and 24 are complimentary to the length of wound closure strips 20, 21, and 22 in that the total end to end length of strips 23 and 24 is slightly less than the length of strips 20, 21, and 22. The positioning of groups of strips of different lengths adjacent to one another permits a user of the wound closure strips to quickly estimate the length of wound closure strip needed for an application. For example, if the user selects a wound closure strip that is too short the user can immediately select the proper size by removing a longer size wound closure strip from the backing card. Consequently, by having groups of multiple lengths of wound closure strips on the backing card the user eliminates the need to cut the wound closure strip to length. In addition cutting a wound closure strip can be difficult since the adhesive on the wound closure strip may adhere to the scissors making the cutting of the wound closure strip very difficult. The present invention with groups of different length wound closure strips arranged on a single backing card is particularly useful in surgical operations such as breast augmentation where three different lengths of wound closure strips are normally used. With the present invention the user eliminates the need to cut the wound closure strips to length since the package contains would closure strips of various lengths that allows the physician to quickly choose the proper length wound closure strip.

Backing card 15 contains a fourth group of wound closure strips 27, 28, 29, and 30 that have a length designated by $L_1$. Note, the placing of the groups of plurality of different length wound closure strips adjacent one another provides a user with an immediate visual comparison of the relative length of the wound closure strips thus allowing a user to quickly estimate the length of the wound closure strip for a particular application. In addition, if the user should not accurately estimate the length of the wound closure strip the user can select and use the next shorter or longer wound closure strip from the backing strip.

Referring to FIG. 4 reference numeral 60 identifies a plurality of groups of different length wound closure strips located on a nonfoldable backing card 61. Backing card contains a first line of weakness 63 on one end and a second line of weakness 62 located in a parallel spaced relationship on the opposite end of backing card 61. Wound closure strips 70, 73, and 74 each have one end extending across a line of weakness 62 and a line of weakness 63.

Wound closure strips 75, 78, and 79 are respectively located in an end to end relationship with wound closure strips 76, 77, and 83. One end of wound closure strips 75, 78, and 79 extends across line of weakness 63 and one end of wound closure strips 76, 77, and 83 extends across line of weakness 62 thus permitting at least one end of the wound closure strips to have an end that can be quickly exposed for ease in attachment of the wound closure strip to a person.

Similarly, wound closure strips 80, 81, and 82 are respectively located in an end to end relationship with wound closure strips 84, 85, and 86. One end of wound closure strips 84, 85, and 86 extends across line of weakness 62 and one end of wound closure strips 80, 81, and 82 extends across line of weakness 63 thus permitting at least one end of the wound closure strips to have an end that can be quickly exposed for ease in attachment of the wound closure strips to a person.

Backing card 61 is shown to illustrate that the wound closure strips of different lengths can be placed on a single non-foldable backing strip.

FIG. 5 shows a cross sectional view of a sterilized package 50 located around the backing card and plurality of wound closure strips shown in FIG. 1. Package 50 typically comprises a sheet of a flexible transparent material 11 and a sheet of a flexible material 12 that permits a user to see the type and length of sutures trips located in the package without opening the package. Typically, one side of package 50 contains a white opaque background for printing information on the product while the other side remains transparent so the user can visually determine the relative size of the wound closure strips in the package. Package 50 contains a peelable seal zone 51 extending around the peripheral region to enclose the wound closure strips in a sterile package. Typically, sheets 11 and 12 are heat sealed together to provide a sterile enclosure for the wound closure strips.

Each of the wound closure strips shown comprises a strip of flexible material having a front side with a layer of adhesive for facing toward the users skin and a backside for facing the users clothing or bandages to act as a protective covering over a wound. The strip of flexible material has a first end with radiused corners and a second end with radiused corners to reduce the tendency of the corners of the wound closure strips of flexible material to pull away from the users skin when the user moves about.

One of the features of the present invention is the positioning of the end of the wound closure strips in a spaced relationship from the edge of the backing sheet to enable storage of unused wound closure strips after the package has been opened. FIG. 1 shows that the rounded ends of the wound closure strips are spaced about ⅛th of an inch from the edge of the backing strip.

The present invention inhibits the drying out of the adhesive on the end of the wound closure strip by spacing the end of the wound closure strip sufficiently far from the edge of the backing sheet so as to inhibit air from entering between the backing sheet and the end of the strip. When the backing strip and the wound closure strip are placed so that the ends of the wound closure strip and the edge of the backing strip are coextensive it apparently causes air to more quickly seep between the wound closure strip and the backing sheet.

A further advantage of the spacing of the wound closure strips from the end of the backing strip is that not only does it inhibit the adhesive on the ends of the strips from drying out during storage, it also prevents the adhesive that may protrude from the end of the wound closure strip from becoming contaminated by foreign materials. That is, often times a person will not use the complete package of wound closure strips. The unused wound closure strips are saved for future use. Since the wound closure strips are no longer in a protective package, the ends of the wound closure strip may come into contact with foreign materials if the end of the wound closure strip extend out to the edge of the backing sheet. Although the wound closure strips are resterilized before use, they may have material on the edge of the strip that makes it difficult for the end of the wound closure strip to properly adhere to the patients skin.

Thus, the spacing of the ends of the wound closure strip from the end of the backing sheet inhibits the adhesive on the end of the wound closure strip from drying out, and thus ensures that wound closure strips that have been stored without a protective sealed package will adhere just as well as those wound closure strips freshly removed from the package. If the adhesive on the end of the wound closure strip dries out and becomes less effective, it may cause the edge of the wound closure strip with the less effective adhesive to come loose when in use. If the end of the wound closure strip comes loose it may cause the entire wound closure strip to be pulled loose by the rubbing of the wound closure strip against the users clothing.

I claim:

1. A package of wound closure strips to quickly enable a user to select the correct length would closure strip by visual inspection of the wound closure strips comprising:
   a single backing sheet for supporting multiple wound closure strips in a side by side unpackaged condition, said backing sheet having a surface for releasing an article adhesively fastened thereto, said backing sheet having a generally rectangular shape with a first end and a second end, said backing sheet including a first line of weakness extending along said first end and a second line of weakness extending along said second end, said first line of weakness permitting a user to tear away said backing sheet along said first line of weakness and said second line of weakness permitting a user to tear away said backing sheet along said second line of weakness;
   a first wound closure strip having a first side, a first end, and a second end, said first wound closure strip having a length L, said first wound closure strip having an adhesive coating extending over said first side of said first wound closure strip and releasably mounting said first wound closure strip to said backing sheet with at least one end of said first wound closure strip extending beyond said first line of weakness to permit the user to tear away said backing sheet along said first line of weakness to expose said first end of said first wound closure strip to permit the user to remove said first wound closure strip from said backing sheet;
   a second wound closure strip having a first side, a first end, and a second end, said second wound closure strip having a length $L_2$, said second wound closure strip having an adhesive coating extending over said first side of said second wound closure strip and releasably mounting said second wound closure strip to said backing sheet with at least one end of said second wound closure strip extending beyond said first line of weakness to permit the user to tear away said backing sheet along said first line of weakness to expose said first end of said second wound closure strip to permit the user to remove said second wound closure strip from said backing sheet; and
   a third wound closure strip having a first side, a first end, and a second end, said third wound closure strip having a length $L_3$, said third wound closure strip having an adhesive coating extending over said first side of said third wound closure strip and releasably mounting said third wound closure strip to said backing sheet with at least one end of said third wound closure strip extending beyond said second line of weakness to permit the user to tear away said backing sheet along said second line of weakness to expose said first end of said third wound closure strip to permit the user to remove said third wound closure strip from said backing sheet where the length $L_2$ of said second wound closure strip and the length $L_3$ of said third wound clousre strip is less than the length L of said first suture strip.

2. The package of wound clousre strips of claim 1 wherein said second wound closure strip and said third wound closure strip are located in an end to end relationship on said backing sheet.

3. The package of wound closure strips of claim 2 wherein said first wound closure strip, said second wound closure strip and said third wound closure strip are located proximate one another on said backing sheet to permit a user to visually compare the length of the strips to one another so that the user can quickly select the proper length wound closure strip for placing over an incision.

4. The package of wound closure strips of claim 3 wherein said ends of said wound closure strips are spaced from said ends of said backing sheet to inhibit air from drying out said adhesive coating on the ends of said wound closure strips.

5. The method of claim 4 including the step of applying said selected wound closure strip perpendicular to the wound.

6. The method of quickly selecting and applying a wound closure strip to an incision without having to cut the wound closure strip to length comprising the steps of:
   opening a package of wound closure strips having an adhesive located along each of the wound closure strips to permit fastening the wound closure strips across a portion of an incision, said package containing a plurality of groups of wound closure strips of different lengths with the plurality of groups of wound closure strips located in a side by side relationship on a backing card to thereby permit a viewer to visually determine the relative lengths of each of the groups of wound closure strips in relationship to each other;
   visually inspecting an incision to determine the approximate length of a wound closure strip for the incision;
   visually inspecting the plurality of groups of wound closure strips of multiple lengths to locate the group of wound closure strips containing the wound closure strip of correct length for the incision;
   removing a first wound closure strip of selected length from the backing card;
   applying the first wound closure strip directly across a portion of the incision without cutting the wound closure strip to length removing a second wound closure strip of selected length from the backing card, applying the second wound closure strip different from the first wound closure strip length directly across a portion of the incision without cutting the second wound closure strip to length.

7. The method of claim 5 including the step of saving unused wound closure strips for future use by storing the unused wound closure strips with the ends of the wound closure strips spaced from the end of the backing card.

8. A package containing a plurality of different length wound closure strips comprising:
- a first transparent panel, said first transparent panel having an outer peripheral edge;
- a second panel, said second panel having an outer peripheral edge, said first transparent panel outer peripheral edge sealed to said second panel along said peripheral edge of said second panel to thereby form a single package for holding a plurality of wound closure strips on a single backing card;
- a backing card having a release agent located thereon to permit removal of adhesive backed articles therefrom, said backing card including a line of weakness to permit tearing said backing card along said line of weakness to thereby expose a portion of an adhesive coated article attached thereto;
- a first group of wound closure strips, said first group of wound closure strips having a first length, each of said wound closure strips of said first group having an adhesive extending thereon to permit each of said wound closure strips of said first group to be adhesively mounted on the skin proximate an incision;
- a second group of wound closure strips, said second group of wound closure strips having a second length, each of said wound closure strips of said second group having an adhesive extending thereon to permit each of said wound closure strips of said second group to be adhesively mounted on the skin proximate an incision said second length less than said first length, said first group of wound closure strips located adjacent to said second group of wound closure strips so that a user can visually compare the length of said first group of wound closure strips and said second group of wound closure strips to permit the user to select the proper length wound closure strip without having to cut the wound closure strip to length.

* * * * *